United States Patent [19]

Brasier

[11] Patent Number: 5,638,957
[45] Date of Patent: Jun. 17, 1997

[54] REUSABLE DIAPER AND WIPE CARRYING CASE

[76] Inventor: Nacole Brasier, 8735 S. Mountain Meadow Dr., West Jordan, Utah 84088

[21] Appl. No.: 678,086

[22] Filed: Jul. 11, 1996

[51] Int. Cl.⁶ .................................................. B65D 69/00
[52] U.S. Cl. .......................... 206/581; 220/531; 220/4.23; 220/339
[58] Field of Search ........................... 206/315.11, 581; 220/4.23, 523, 526, 531, 554, 339

[56] References Cited

U.S. PATENT DOCUMENTS

| | | | |
|---|---|---|---|
| D. 174,914 | 6/1955 | McGee | 206/315.11 |
| 1,610,146 | 12/1926 | Panzer | 220/523 |
| 2,501,270 | 3/1950 | Fleming | 206/315.11 |
| 4,154,323 | 5/1979 | Sneider | 190/2 |
| 4,221,221 | 9/1980 | Ehrlich | 128/284 |
| 4,574,822 | 3/1986 | Helinsky | 132/79 R |
| 4,702,378 | 10/1987 | Finkel et al. | 206/581 |
| 4,821,751 | 4/1989 | Chen | 206/581 |
| 4,832,193 | 5/1989 | Kime | 206/315.11 |
| 5,046,620 | 9/1991 | Barabino | 206/581 |
| 5,062,557 | 11/1991 | Mahvi et al. | 224/153 |
| 5,261,531 | 11/1993 | Nieves | 206/205 |
| 5,443,161 | 8/1995 | Jonese | 206/581 |
| 5,462,192 | 10/1995 | Pomroy et al. | 220/523 |

*Primary Examiner*—David T. Fidei
*Attorney, Agent, or Firm*—Workman, Nydegger & Seeley

[57] ABSTRACT

A reusable diaper and wipe carrying case includes a first housing having an interior surface defining a chamber for holding premoistened baby wipes. The case further includes a second housing having an interior surface defining a chamber for holding one or more diapers. A partition wall is positioned between the access opening of the first housing and the access opening of the second housing. The first housing, second housing, and partition wall are hingedly connected at an outside edge to permit independent closing and opening to the wipe chamber and diaper chamber. Ridges are also formed on one side of the partition wall to produce an airtight seal between the partition wall and the access opening of the first housing.

19 Claims, 2 Drawing Sheets

5,638,957

REUSABLE DIAPER AND WIPE CARRYING CASE

BACKGROUND OF THE INVENTION

1. The Field of the Invention

The present invention relates to cases for holding and storing both diapers and premoistened wipes needed for changing a baby's diaper and, more specifically, cases for holding the diapers and wipes in discrete compartments.

2. Description of the Prior Art

Parents and others responsible for infants and small children regularly and in every conceivable location need a reliable supply of both diapers and wipes. This requirement has given rise to numerous inventions allowing different baby supplies to be transported.

The most common examples of such an apparatus are standard diaper bags. Diaper bags are typically large, flexible, cloth bags with multiple compartments capable of carrying food, bottles, toys, diapers, wipes, lotions, powders, and any other accessories needed by a child. While these bags are useful to parents, they have their drawbacks. For examples, cloth bags are easily torn, and quickly become dirty from spilled milk, food, and dirty diapers or cloths. Due to the many compartments, it can also be difficult to thoroughly clean the bag.

Furthermore, since diaper bags do not typically include an airtight pocket, premoistened wipes which are commonly used in changing a baby's diaper must either be carried in their original container, which is typically relatively large, or must be transferred to another airtight container which is then placed within the diaper bag. Additionally, diaper bags are typically so large that on those times where only the essentials of a couple of diapers and some wipes are needed, conventional diaper bags become impractical and burdensome.

To help remedy the burden of always carrying a large bag, several recent inventions use disposable baby change kits such as those described by U.S. Pat. No. 5,443,161 issued to Jonese, and U.S. Pat. No. 4,702,378 issued to Finkel et al. The Jonese patent discloses a disposable kit having what it calls a plurality of baby products sufficient for two complete diaper changes. The Finkel patent discloses a single use disposable baby change kit. The kit is made from a thin plastic film folded over upon itself so that the wipes and diaper are enveloped within the kit and protected along with other baby products such as powder, soap and coupons. While these inventions do help solve the problems associated with large diaper bags, they are still not ideal in every situation and do not represent the most cost effective solution.

Often a baby does not require lotion, powder, or other baby care products. Any disposable kit containing such products would simply waste the additional products and their associated cost.

Additionally, if a child is extremely dirty a disposable kit may not contain sufficient wipes. A second kit would thus have to be used. Also, if a kit contains sufficient materials for multiple diapers, and only one is needed, then the additional wipes could easily dry out prior to the kit's use a second time.

Because diapers and wipes are typically cheapest when purchased in bulk, most households already have an ample supply of both on hand. Thus, what is really needed is not, a plurality of discrete single use kits, but a way to hold a desired amount of diapers and wipes.

Also, as babies grow, different size diapers are needed, thus making kits for small infants unsuitable for use with a toddler. This in turn increases costs because different kit sizes must be manufactured for each size of baby. Moreover, the fact that the kits are disposable means that they must be repurchased each time one is needed.

Finally, since these disposable kits are made of thin plastic film, they are less capable of being stored in any location where they would be subjected to any kind of force which could puncture or rip the thin plastic skin.

OBJECTS AND SUMMARY OF THE INVENTION

Accordingly, it is an object of the present invention to provide new and improved small, compact containers capable of holding both wet wipes and diapers that can be easily carried by parents and others who care for small children.

It is a further object of the present invention to provide containers which allow for individual optimization of the number and kind of desired wet wipes and diapers positioned within the containers so as to reduce waste and cost.

It is another object of the invention to provide containers capable of easy cleaning and which can be reused multiple times.

It is yet another object of the invention to provide containers with an airtight compartment capable of keeping premoistened wipes wet for a long period of time and allowing for long term emergency storage of the containers in almost any location.

It is yet another object of the invention to provide a container strong enough to withstand tearing and puncturing forces which will allow the container to be handled and stored without concern in such places as a car trunk.

To achieve the foregoing objectives and in accordance with the invention as broadly disclosed and claimed herein, a reusable diaper and wipe carrying case is provided. The carrying case has a rigid first housing with a wipe chamber for storing a select number of premoistened wipes, a rigid second housing with a diaper chamber for storing a select number of diapers, and a partition wall positioned therebetween. The partition wall is configured to selectively close off the wipe chamber and the diaper chamber.

When closed, the wipe chamber forms an air tight and moisture impermeable compartment. As a result, premoistened wipes can be housed within the wipe chamber for long periods of time without drying out. The air tight wipe chamber also enables the premoistened wipes to be purchased in cost effective bulk quantity, yet be carried around in the present case in small useable numbers without drying out.

The diaper chamber is preferably sized to fit between 1–3 diapers. The inventive carrying case also allows the diapers to be purchased in cost effect bulk quantities, but enables diapers of different sizes or quantity to be easily carried or stored for an intended use.

A hinge interconnects the first housing, the second housing, and the partition wall to enable the wipe chamber and the diaper chamber to be individually, selectively opened. Attachment means are also provided for releasably connecting the partition wall to the first housing and the second housing.

The above and still further objects of the present invention will become apparent upon consideration of the following detailed description of the preferred embodiment, especially when taken in conjunction with the accompanying drawings.

BRIEF DESCRIPTION OF THE DRAWINGS

In order that the manner in which the above-recited and other advantages and objects of the invention are obtained will be understood, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

Figure 1:
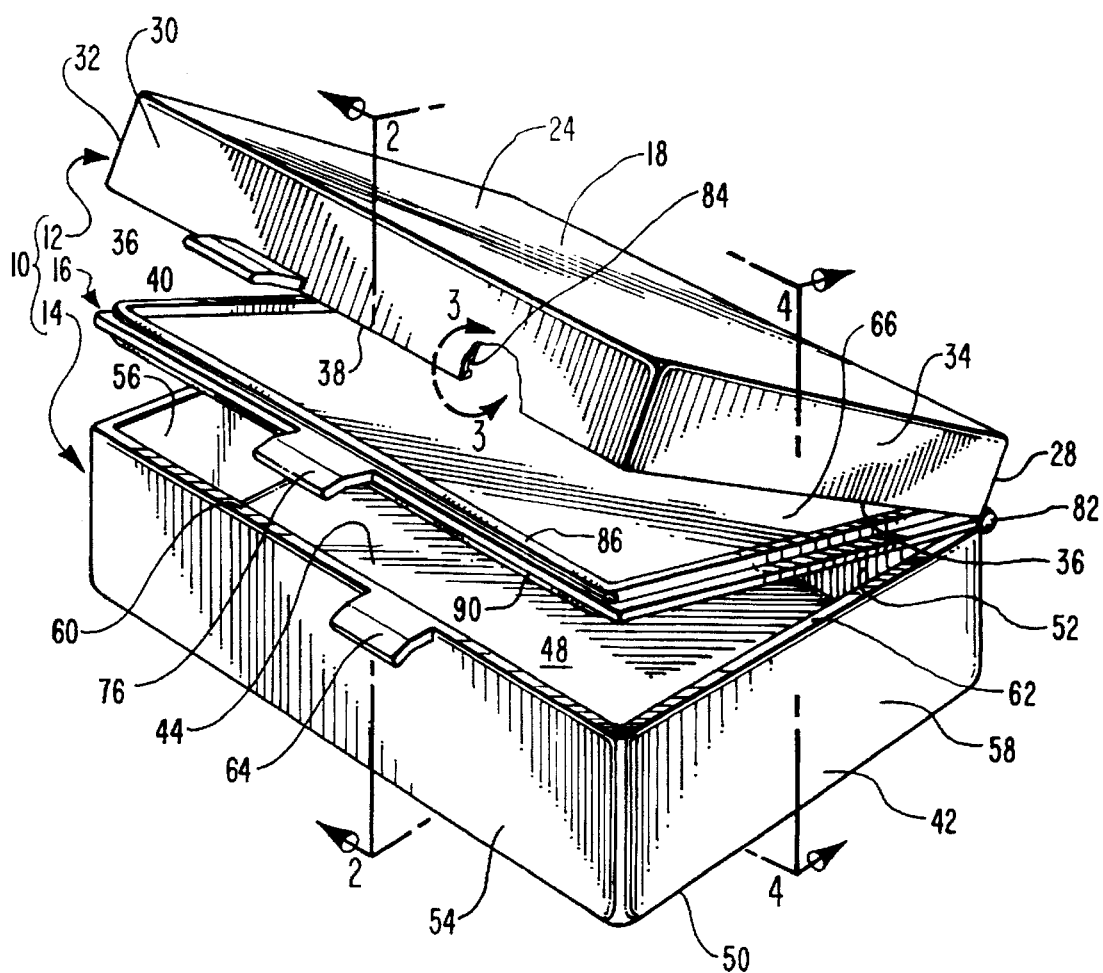
FIG. 1 is a perspective view of a reusable diaper and wipe carrying case.

Depicted in FIG. 1 is a perspective view of one preferred embodiment of an inventive reusable diaper and wipe carrying case 10. Carrying case 10 is shown as generally comprising a first housing 12, a second housing 14, and a partition wall 16 positioned therebetween. First housing 12, second housing 14, and partition wall 16 are preferably molded from a plastic that rigidly sets. Such a material enables carrying case 10 to be cheaply manufactured, easily cleaned, and resistant to puncture, tearing, or impact. Of course, an alternative embodiment, carrying case can be made from alternative materials such as wood, metal, or composites.

Figure 2:
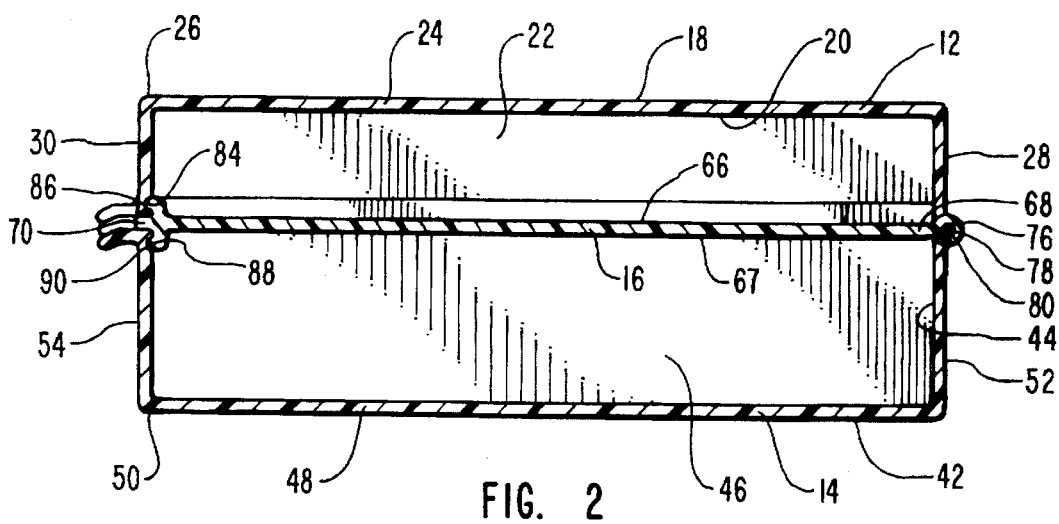
FIG. 2 is an elevated cross-sectional side view of the reusable diaper and wipe carrying case shown in FIG. 1 taken along sections lines 2—2 shown thereof.

Referring to both FIGS. 1 and 2, first housing 10 generally comprises an exterior surface 18 and an interior surface 20. Interior surface 20 defines a wipe chamber 22 for selectively housing a plurality of premoistened baby wipes. First housing 12 is more specifically defined as comprising a roof 24 having an outside perimeter 26. A back wall 28, a front wall 30, and opposing side walls 32 and 34 each orthogonally projecting from outside perimeter 26 to an outside edge 36. Outside edge 36 cumulatively defines an access opening 38 for wipe chamber 22. Finally, projecting outwardly from front wall 30 near outside edge 36 is a first tab 40 which will be discussed later in greater detail.

Also depicted in FIGS. 1 and 2 is second housing 14. Second housing 14 is likewise shown as comprising an exterior surface 42 and an interior surface 44. Interior surface 44 defines a diaper chamber 46 sized to hold a select number of diapers, typically between about one to three diapers. Since diapers are larger than wipes, second housing 14 is typically larger than first housing 12. Second housing 14 is further shown as comprising a floor 48 having an outside perimeter 50. A back wall 52, a front wall 54, and a pair of opposing side walls 56 and 58 each orthogonally project from outside perimeter 50 to an outside edge 60. Outside edge 60 cumulatively defines an access opening 62 to diaper chamber 46. Second housing 14 further includes an outwardly projecting second tab 64 extending from front wall 54 near outside edge 60.

Figure 4:
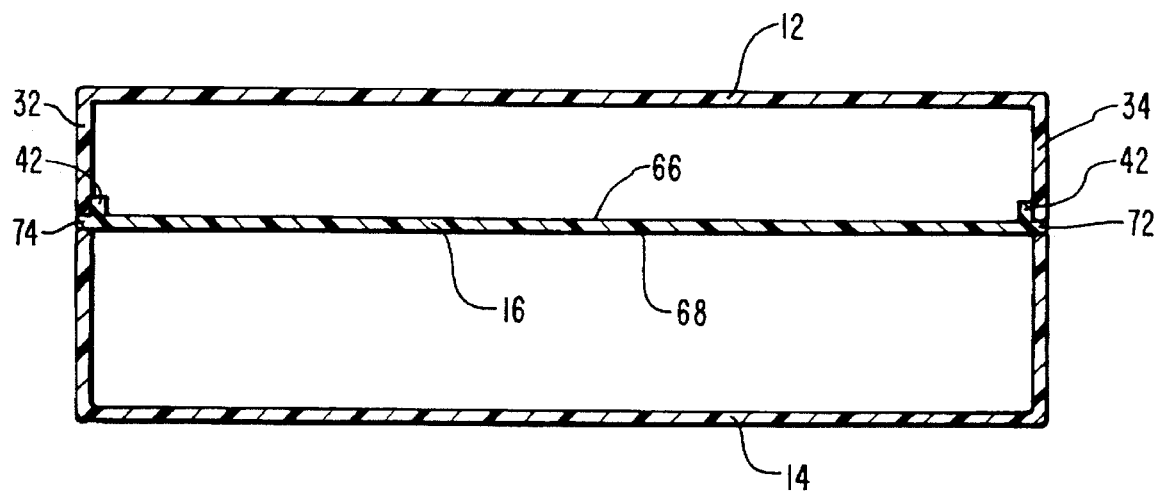
FIG. 4 is an elevated cross-sectional front view of the reusable diaper and wipe carrying case shown in FIG. 1 taken along section lines 4—4 thereof.

FIGS. 1 and 2 further depict partition wall 16 positioned between first housing 12 and second housing 14. Partition wall 16 is shown as comprising a first side 66 facing wipe chamber 22 of first housing 12 and an opposing second side 68 facing diaper chamber 46 of second housing 14. Partition wall 16 further includes a back edge 68, a front edge 70 and, as best depicted in FIG. 4, opposing side edges 72 and 74. Referring back to FIG. 1, projecting from front edge 60 is a third tab 76.

The present invention provides means for hingedly connecting first housing 12, second housing 14, and partition wall 16 to enable each of the first housing 12, second housing 14, and partition wall 16 to independently rotate relative to each other. By way of example and not by limitation, depicted in FIG. 2 is a tubular member 76 attached to back edge 68 of partition wall 16. Tubular member 76 has a passageway 78 longitudinally extending therethrough. Constructed in a similar fashion, although not specifically shown in the attached drawings, a tubular member 76 is also formed at outside edge 36 of back wall 28 of first housing 12 and at outside edge 60 of back wall 52 of second housing 14. Each tubular member 76 has a passageway 78 longitudinally extending therethrough. Furthermore, each tubular member 76 is staggered on first housing 12, second housing 14, and partition wall 16 so that each passageway 78 can be longitudinally aligned. In this position, a pin 80 is inserted within each passageways 78 to form a hinge 82. Hinge 82 interconnects first housing 12, second housing 14, and partition wall 16 in an independently rotatable fashion.

The present invention envisions that a plurality of alternative embodiments exist for the means for hingedly connecting the first housing, the second housing, and the partition wall. Alternative structures include integrally molding first housing 12, second housing 14, and partition wall 16 so that a thin, flexible piece of plastic interconnects each of the components. Alternatively, a variety of different conventional hinged structures could be used in various configurations to independently interconnect first housing 12, second housing 14, and partition wall 16. In yet another alternative embodiment, flexible straps or strips of material could also be interconnected between the components to enable hinged attachment therebetween.

As a result of the attachment of hinge 82, partition wall 16 can be rotatably biased against first housing 12 so as to substantially cover access opening 38 while access opening 62 of second housing 14 remains open. Alternatively, partition wall 16 can be biased against second housing 14 so as to substantially cover access opening 62 while access opening 38 of first housing 12 remains opened. Finally, as shown in FIG. 2, carrying case 10 can be completely closed so that partition wall 16 is biased between first housing 12, and second housing 14.

Figure 3:
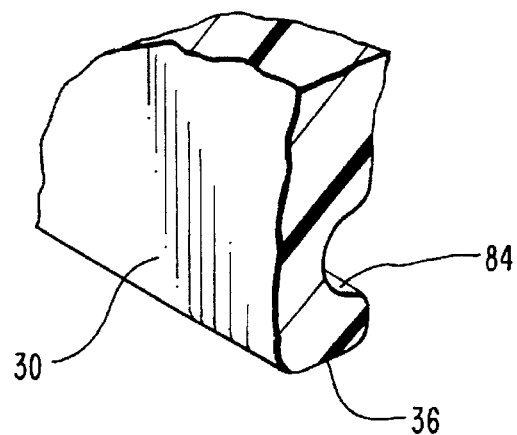
FIG. 3 is an enlarged perspective view of a portion of the reusable diaper and wipe carrying case shown in FIG. 1 taken along section lines 3—3 thereof.

The present invention also provides first attachment means for releasably connecting partition wall 16 to first housing 12. By way of example and not by limitation, depicted in FIGS. 1 and 3 is an elongated first groove formed on the inside surface of first wall 30 of first housing 12. First groove 84 substantially extends between opposing side walls 32 and 34 of first housing 12. Furthermore, an L-shaped first locking ridge 86 projects from first side 66 of partition wall 16 near first edge 70. First locking ridge 86 is configured and positioned such that as partition wall 16 is biased against first housing 12, first locking ridge 86 is received and biased within first groove 84 to hold first housing 12 and partition wall 16 in a manually separatable engagement. First tab 40 and third tab 76 are used for manually attaching and separating first housing 12 and partition wall 16.

The present invention also provides second attachment means for releasably connecting partition wall 16 to second housing 14. By way of example and not by limitation, one embodiment of the second attachment means comprises an elongated second groove formed on the interior surface of front wall 54 adjacent to outside edge 60 as shown in FIG. 2. In addition, an L-shaped second locking ridge 90 projects from second side 67 of partition wall 16 near front edge 70. As partition wall 16 is biased against second housing 14, second locking ridge 90 is received and biased within second groove 88 to hold partition wall 16 and second housing 14 in a manually separatable fashion. Second tab 64 and third tab 76 are used for manually connecting and disconnecting partition wall 16 from second housing 14.

The present invention also envisions that the first attachment means and the second attachment means can include a variety of well known connecting structures. For example, the first and second attachment means could comprise any one of a variety of well known latches, hooks, tongue and groove configurations, overlapping friction based parts, and other locking structures.

Finally, the present invention also provides sealing means for effecting a substantially airtight seal between partition wall 16 and access opening 38 of first housing 12. By way of example and not by limitation, one embodiment of the sealing means includes an elongated first sealing ridge 92 projecting from first side 66 near side edge 72 and longitudinally extending between first locking ridge 86 and back edge 68 of partition wall 16. Likewise, a second sealing ridge 94 projects from first side 66 of partition wall 16 near side edge 74 and also longitudinally extends between first locking ridge 86 and back edge 68 of partition wall 16. As shown in FIG. 4, as partition wall 16 is biased against first housing 12, first sealing ridge 92 is biased against the interior surface of side wall 34 and second sealing ridge 94 is biased against the interior surface of side wall 32, thereby affecting a substantially airtight seal therebetween. Furthermore, first locking ridge 86 received within groove 84 also forms a substantially airtight seal therebetween. As such, wipe chamber 22 forms a substantially airtight chamber. This configuration permits disposable wipes to be positioned within wipe chamber 22 for long periods of time without becoming dried out.

The present invention also envisions that a variety of alternative structures could be used for the sealing means. By way of example, alternative structures of the sealing means can include positioning a gasket material between partition wall 16 and first housing 12. Furthermore, interlocking ridges and grooves could be formed on opposing partition wall 16 and first housing 12. Finally, a number of alternative lip configurations could be formed on partitional 16 in first housing 12 which would overlap to form a substantially sealed connection between partion wall 16 and first housing 12.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A reusable diaper and wipe carrying case comprising:
   (a) a first housing having an interior surface defining a wipe chamber and an outside edge defining an access opening to the wipe chamber;
   (b) a second housing having an interior surface defining a diaper chamber and an outside edge defining an access opening to the diaper chamber, the second housing being hingedly connected to the first housing to enable the access opening of the first housing to selectively face the access opening of the second housing; and
   (c) a partition wall hingedly disposed between the first housing and the second housing, the partition wall having a first side configured to be selectively biased against the access opening of the first housing to enclose the wipe chamber, the partition wall also having a second side configured to be selectively biased against the access opening of the second housing to substantially enclose the diaper chamber.

2. A reusable diaper and wipe carrying case as recited in claim 1, further comprising sealing means for effecting a substantially air tight seal between the partition wall and the access opening of the first housing.

3. A reusable diaper and wipe carrying case as recited in claim 2, wherein the sealing means comprises a ridge projecting from the first side of the partition wall, the ridge being biased against the interior surface of the first housing when the partition wall is biased against the access opening of the first housing.

4. A reusable diaper and wipe carrying case as recited in claim 1, further comprising first attachment means for releasably connecting the partition wall to the first housing.

5. A reusable diaper and wipe carrying case as recited in claim 4, wherein the first attachment means comprises:
   (a) a first receiving groove formed on the interior surface of the first housing; and
   (b) a first finger projecting from the first side of the partition wall, the first finger being configured to be received and biased within the first receiving groove when the partition wall is biased against the access opening of the first housing.

6. A reusable diaper and wipe carrying case as recited in claim 1, further comprising second attachment means for releasably connecting the partition wall to the second housing.

7. A reusable diaper and wipe carrying case as recited in claim 6, wherein the second attachment means comprises:
   (a) a second receiving groove formed on the interior surface of the second housing; and
   (b) a second finger projecting from the second side of the partition wall, the second finger being configured to be received and biased within the second receiving groove when the partition wall is biased against the access opening of the second housing.

8. A reusable diaper and wipe carrying case as recited in claim 1, wherein the first housing and the second housing are rigid.

9. A reusable diaper and wipe carrying case as recited in claim 1, wherein the first housing, the second housing, and the partition wall each have a tab projecting therefrom.

10. A reusable diaper and wipe carrying case comprising:
    (a) a rigid first housing having an interior surface defining a wipe chamber and an outside edge defining an access opening to the wipe chamber;
    (b) a rigid second housing having an interior surface defining a diaper chamber and an outside edge defining an access opening to the diaper chamber;
    (c) a partition wall disposed between the access opening of the first housing and the access opening of the second housing, the partition wall having a first side configured to substantially cover the access opening of the first housing and a second side configured to substantially cover the access opening of the second housing;

(d) means for hingedly connecting the first housing, the second housing, and the partition wall to enable each of the first housing, the second housing, and the partition wall to independently rotate relative to each other; and (e) sealing means for effecting a substantially air tight seal between the partition wall and the access opening of the first housing.

11. A reusable diaper and wipe carrying case as recited in claim 10, wherein the means for hingedly connecting comprises:

(a) a tubular member individually attached to each of the first housing, second housing and partition wall, each tubular member having a passageway longitudinally extending therethrough, each tubular member also being configured so that each passageway of each tubular member can be axially aligned; and (b) a pin disposed through the axially aligned passageway of each of the tubular members.

12. A reusable diaper and wipe carrying case as recited in claim 10, wherein the sealing means comprises a ridge projecting from the first side of the partition wall, the ridge being biased against the interior surface of the first housing when the partition wall is biased against the access opening of the first housing.

13. A reusable diaper and wipe carrying case as recited in claim 10, further comprising first attachment means for releasably connecting the partition wall to the first housing.

14. A reusable diaper and wipe carrying case as recited in claim 13, wherein the first attachment means comprises:

(a) a first groove formed on the interior surface of the first housing; and (b) an L-shaped first locking ridge projecting from the first side of the partition wall, the first locking ridge being configured to be received and biased within the first groove when the partition wall is biased against the access opening of the first housing.

15. A reusable diaper and wipe carrying case as recited in claim 10, further comprising second attachment means for releasably connecting the partition wall to the second housing.

16. A reusable diaper and wipe carrying case as recited in claim 15, wherein the second attachment means comprises:

(a) a second groove formed on the interior surface of the second housing; and (b) an L-shaped second locking ridge projecting from the second side of the partition wall, the second locking ridge configured to be received and biased within the second groove when the partition wall is biased against the access opening of the second housing.

17. A reusable diaper and wipe carrying case as recited in claim 10, wherein the first housing and the second housing are rigid.

18. A reusable diaper and wipe carrying case as recited in claim 10, wherein the first housing, the second housing, and the partition wall each have a tab projecting therefrom.

19. A reusable diaper and wipe carrying case as recited in claim 10, wherein the first housing, the second housing, and the partition wall are each made of plastic.

* * * * *